(12) United States Patent
Morris et al.

(10) Patent No.: US 7,016,723 B2
(45) Date of Patent: Mar. 21, 2006

(54) RATE ADJUSTABLE DRUG DELIVERY SYSTEM

(75) Inventors: Russell L. Morris, Lindstrom, MN (US); Carter R. Anderson, Eagan, MN (US)

(73) Assignee: Birch Point Medical, Inc., Oakdale, MN (US)

( * ) Notice: Subject to any disclaimer, the term of this patent is extended or adjusted under 35 U.S.C. 154(b) by 683 days.

(21) Appl. No.: 10/162,473

(22) Filed: Jun. 3, 2002

(65) Prior Publication Data
US 2002/0188241 A1   Dec. 12, 2002

Related U.S. Application Data

(63) Continuation-in-part of application No. 09/613,984, filed on Jul. 11, 2000, now Pat. No. 6,421,561.

(60) Provisional application No. 60/173,710, filed on Dec. 30, 1999.

(51) Int. Cl.
*A61N 1/30* (2006.01)
(52) U.S. Cl. .................................... 604/20
(58) Field of Classification Search ............ 607/2; 604/20
See application file for complete search history.

(56) References Cited

U.S. PATENT DOCUMENTS

| 116,562 A | 7/1871 | Collins |
|---|---|---|
| 175,974 A | 4/1876 | Hall |
| 222,276 A | 12/1879 | Hunter |
| 385,556 A | 7/1888 | Hoke |
| 393,741 A | 12/1888 | Collins |
| 770,014 A | 9/1904 | Linn |
| 857,664 A | 6/1907 | Overman |
| 4,035,554 A | 7/1977 | Halberstadt et al. |
| 4,619,252 A | 10/1986 | Ibbott |
| H178 H | 12/1986 | Biggar |
| 4,626,482 A | 12/1986 | Hamlen et al. |
| 4,713,050 A | 12/1987 | Sibalis |
| 4,722,726 A | 2/1988 | Sanderson et al. |
| 4,747,819 A | 5/1988 | Phipps et al. |
| 4,752,285 A | 6/1988 | Petelenz et al. |
| 4,767,401 A | 8/1988 | Seiderman |
| 4,927,408 A | 5/1990 | Haak et al. |
| 4,950,229 A | 8/1990 | Sage, Jr. |
| 5,135,477 A | 8/1992 | Untereker et al. |
| 5,160,315 A | 11/1992 | Heinecke et al. |
| 5,162,042 A | 11/1992 | Gyory et al. |
| 5,201,924 A | 4/1993 | Mix et al. |
| 5,203,768 A | 4/1993 | Haak et al. |
| 5,221,254 A | 6/1993 | Phipps |
| 5,254,081 A | 10/1993 | Maurer et al. |
| 5,295,979 A | 3/1994 | DeLaurentis et al. |
| 5,298,017 A | 3/1994 | Theeuwes et al. |
| 5,320,731 A | 6/1994 | Muller et al. |

(Continued)

FOREIGN PATENT DOCUMENTS

DE   1967927   7/1934

(Continued)

OTHER PUBLICATIONS

"Transdermal Iontophoresis. Part I: Basic Principles and Considerations", Methods Find Exp Clin Pharmacol, 1999, 21(2): 139-151.

*Primary Examiner*—Mark Bockelman
(74) *Attorney, Agent, or Firm*—Nikolai & Mersereau, P.A.; C. G. Mersereau

(57) ABSTRACT

A transdermal iontophoretic therapeutic agent delivery system which is provided with a plurality of self-contained serially connected galvanic sources.

30 Claims, 8 Drawing Sheets

U.S. PATENT DOCUMENTS

| | | |
|---|---|---|
| 5,322,520 A | 6/1994 | Milder |
| 5,354,321 A | 10/1994 | Berger |
| 5,356,632 A | 10/1994 | Gross et al. |
| 5,358,483 A | 10/1994 | Sibalis |
| 5,403,275 A | 4/1995 | Phipps |
| 5,405,317 A | 4/1995 | Myers et al. |
| 5,431,625 A | 7/1995 | Fabian et al. |
| 5,436,090 A * | 7/1995 | Kono et al. ............ 429/317 |
| 5,458,569 A | 10/1995 | Kirk, III et al. |
| 5,466,217 A | 11/1995 | Myers et al. |
| 5,533,971 A | 7/1996 | Phipps |
| 5,605,536 A | 2/1997 | Sibalis |
| 5,651,768 A | 7/1997 | Sibalis |
| 5,685,837 A | 11/1997 | Horstmann |
| 5,759,564 A | 6/1998 | Milder et al. |
| 5,772,688 A | 6/1998 | Muroki |
| 5,983,130 A | 11/1999 | Phipps et al. |

FOREIGN PATENT DOCUMENTS

| | | |
|---|---|---|
| DE | 2263792 | 3/1974 |
| EP | 0060451 | 3/1982 |
| EP | 0308572 | 8/1984 |
| EP | 456 122 | 5/1991 |
| EP | 0 893 139 | 7/1998 |
| EP | 0 893 139 A | 1/1999 |
| FR | 2 263 792 A | 10/1972 |
| FR | 2 263 792 A | 10/1975 |
| GB | 410009 | 5/1934 |
| GB | 2.206493 | 1/1989 |
| GB | 0456122 | 11/1995 |
| WO | WO 01/49365 | 7/2001 |

* cited by examiner

RATE ADJUSTABLE DRUG DELIVERY SYSTEM

This application is a continuationin-part of complete application Ser. No. 09/613,984, filed Jul. 11, 2000, now U.S. Pat. No. 6,421,561, issued Jul. 16, 2002, and incorporated herein by reference in its entirety, claiming priority based on provisional application number 60/173,710, filed Dec. 30, 1999, and entitled "Rate Adjustable Drug Delivery System". Cross-reference is also made to a corresponding patent application Ser. No. 10/166157, filed Jun. 10, 2002, pending published Feb. 6, 2003 as 2002/0028170 Al, and PCT US00/27301, filed Oct. 4, 2000, published Jul. 12, 2001 as WO 01/49365, both of which claim the benefit of the above-mentioned provisional application.

BACKGROUND OF THE INVENTION

I. Field of the Invention

The present invention concerns transdermal delivery of therapeutic agents by use of an applied electromotive force, commonly known as iontophoresis. The system is contained preferably in a rather small skin worn patch which contains electrodes and a therapeutic agent. When applied to the skin, the system completes a circuit and spontaneously initiates the flow of a galvanic current. More particularly, the invention is directed to a capacity-related power source/dosage characterization technique for iontophoresis. The power sources/dosage control systems are based on combinations of a plurality of galvanic couple power sources selected from manufactured lots or batches of such power sources or source components of tested capacity so that each system capacity can also be designated on labels. The system is self contained and the delivery rate may be variable or adjustable.

II. Related Art

The process of iontophoresis was described by LeDuc in 1908, and has since found wide spread acceptance and commercial use in the delivery of ionically charged therapeutic compounds such as pilocarpine, dexamethasone, and lidocaine. In this delivery method, ions bearing a positive charge are driven across the skin at the site of an electrolytic electrical system anode, while ions bearing a negative charge are driven across the skin at the site of an electrolytic electrical system cathode.

With iontophoretic devices, the application time and level of current flow (usually reported in units of milliamp minutes) between the anode and cathode is directly correlated to the amount of drug delivered. The efficiency of drug delivery in an iontophoretic system can be measured by the proportion of current carried by the drug molecule, relative to the current carried by competing non-medication ions.

Iontophoresis devices have conventionally comprised two electrodes attached to a patient, each connected via a wire to a microprocessor controlled electrical instrument. Medication is placed under one or both of the electrodes, for delivery into the body as the instrument is activated. The instrument is designed to regulate current flow and application time. Examples of such instruments are described in U.S. Pat. Nos. 5,254,081, and 5,431,625. Power for these devices is usually provided by DC batteries, which when providing power for the microprocessor controlled circuitry allow application of a voltage to the electrodes to create a regulated current flow. The automated control of current flow and time (milliamp-minutes) is of great advantage, in order to prevent excessive dosages of therapeutic agents from being delivered. However, these battery powered microprocessor systems are disadvantaged by the fact that patients are 'attached by wire' to an instrument, which limits patient mobility and ability to conduct normal daily activities. A typical application period is approximately 20 minutes to 2 hours, which consumes instrument, caregiver, and patient time.

A significant advantage of a microprocessor controlled iontophoretic system is an ability to adjust electrical current as a function of time, while the system is being used. For example, to administer medication quickly into systemic circulation, an initial high flow rate is desired. However, adjustment to a lower flow rate may be desired afterward for optimal maintenance of a particular plasma medication level.

More recently, wearable iontophoretic systems have been developed in which the electrical circuitry and power supplied are integrated into a single patch. These systems are advantageous in that they do not require external wires, and they are much smaller in size. Examples of such systems can be found in U.S. Pat. Nos. 5,358,483; 5,458,569; 5,466,217; 5,605,536; and 5,651,768. However, these systems also have drawbacks. They are relatively inflexible and expensive, owing to the requirements of multiple electronic components, battery power supplies and electrical interconnects.

Power to drive iontophoretic current flow can also be supplied by galvanic means, which utilizes dissimilar anode and cathode materials to produce a spontaneous current flow when they are contacted with the body. These systems hold advantage, in that separate electrical circuitry and battery sources are not required. An iontophoretic device, not of the transdermal type, but one which utilizes galvanic means is described in U.S. Pat. No. 5,322,520, which describes an implanted device designed to deliver oligodynamic metal ions from its surface, in order to kill bacteria on or near it.

Devices suggesting galvanic power as a means to transdermally deliver medication are described in U.S. Pat. Nos. 5,162,042, and 5,405,317. These devices are disadvantaged by the fact that the amount of medication delivered is not automatically regulated, and they require a timely removal of the device from the body to prevent a potentially toxic over- dosage of medication.

In a co-pending application PCT/US99/18861, designating the U.S., claiming priority based on U.S. provisional application No. 60/098,652, assigned to the same Assignee as the present application, an iontophoresis patch system is described which uses galvanic power and provides a known dosage capacity. Thus, this system can be designed to automatically shut off after a specified dosage, and the risk of overdosage is eliminated. That co-pending application is deemed incorporated herein by reference for any purpose.

Horstmann, in U.S. Pat. No. 5,685,837, describes a transdermal therapeutic system which uses series mounted sheet-like galvanic elements as a power source. That device has an ability to either create a constant intensity of current using a high internal resistance element, or create a gradual decreasing current intensity using a low internal resistance element. The low internal resistance, and a decreasing current flow, is caused by a build up of ions into an electrolyte layer of the galvanic element.

While it appears advantageous, there are certain practical disadvantages to the Horstmann system. To achieve a decreasing current, a very thin electrolyte layer required. The thin layer is susceptible to mechanical failure during production or use. Also, rather than the gradual decreasing current of the Horstmann system, a steady high rate of current which then rapidly falls is optimal, so that a known charge dosage can be administered in minimal time. The actual charge dosage administered using the Horstmann device is not accurately known, since a nernstian decline in voltage is in a non-linear diminishing rate, and thus the system will not fall to zero current during practical time scales.

One restriction of all galvanic systems is a limited supply of user-friendly materials which can be practically used. Many materials may be toxic themselves, and/or they may be difficult to work with in the manufacturing process. A significant problem lies with materials that are reactive with water, and therefore can alter the pH of the medication solution during use. pH changes can harm skin, or cause adverse reaction with medication. For example, we have found zinc ($E^0=-0.763$) to be an excellent galvanic material, but magnesium ($E^0=-2.37$) causes a pH change in iontophoretic medication chambers. Silver chloride ($E^0=+0.222$) does not affect pH of a medication chamber, but manganese dioxide ($E^0=+1.23$) does. Consequently, the voltages obtainable in galvanically powered systems are limited by material stability or compatibility. Of course, various other species may have application as oxidizable or reducible species under different circumstances.

Another restriction or limitation of galvanically powered systems is an inability to increase or decrease voltage (and medication delivery) during use. The voltage is fixed by the galvanic half reactions used, and cannot be altered in process. This is a significant disadvantage in circumstances where increasing rate of delivery, such as to administer a bolus of medication, is desired. Accordingly, it would present a great advantage were increased potential available in such a device.

At a given potential, the rate that medications are introduced is a function of the level of current while the total quantity of medication delivered is a function of both current levels and the time, i.e., the amount of total charge transferred. Because of this relation, the quantity of medication introduced by iontophoresis is often referred to in units of mA-minutes of dosage. Thus, for example, an equivalent 40 mA-minute dosage can be delivered at different rates; 0.1 mA for 400 minutes, 1 mA for 40 minutes, 10 mA for 4 minutes, etc. Labeling, of course, can also be in units of charge (coulombs in addition to mA-minutes), equivalent amount of drug (mass, moles), time (hours), amount of electrode material (mass, moles), or other units that relate to total charge capacity of the galvanic couple power source or other battery that gets delivered.

Control of the dosage delivered by iontophoresis is usually accomplished by means of electrical circuitry in the form of electrical components mounted on the circuit layer. Electrical components can be utilized to regulate the level, waveform, timing and other aspects of the electrical current and the system usually also includes a microprocessor adapted to control the current over time. These electrical circuits are well known and are described, for example, in U.S. Pat. No. 5,533,971.

It is well known in manufacturing piece parts that costs are reduced by production in high volume, typically large batch (or lot) quantities. However, it has been discovered that mass production of iontophoretic power supplies to deliver a fixed, pre-determined charge or dosage within close tolerances is difficult to accomplish. In producing large batch quantities, there inevitably exists variability associated with the manufacturing process. Thus, for example, the actual capacity of power supplies produced and so the associated dosage produced in a manufacturing lot often deviates somewhat from the capacity intended (or "target") dosages. This is not totally unexpected inasmuch as iontophoretic devices of the class are generally designed to optimally deliver a fixed and known charge in a range between about 0.06 and 60 coulombs, which corresponds to between 0.00000062 and 0.00062 gram equivalent weights of oxidizable or reducible species in limiting supply. Clearly, consistency at these low amounts is a challenge.

Additionally, it has been discovered that drift can occur during processing to cause a segment of a lot to deviate from the rest. For example, in building a sequence of parts which constitute a manufacturing lot, nominally between 1,000 and 1,000,000 parts, a first portion of the lot may deviate from a middle or end portion. Even when several devices are prepared in a single manufacturing step, deviations can occur between groupings.

III. Advantages of the Invention

The invention provides galvanically powered iontophoretic devices and methods of making same in which the devices have a power source/dosage control system of reliable capacity which can be labeled and which, by combining components in a desired fashion, can provide any desired time-voltage profile (and consequently customize the rate profile of medication delivery). The devices of the present invention eliminate the need for any microprocessor or human intervention to administer the indicated dosage.

The present invention further provides a solution to overcome the idiosynchroses of manufacture in each lot or batch of galvanic couple power sources or source components by providing a special lot testing technique which characterizes the capacity of the power sources or source components and, in turn, enables dosage capacity to be predicted with a much greater degree of accuracy. This enables the dosage to be designated or labeled on a corresponding device and further enables the power source to, in addition to providing the sole source of power, provide the only dosage control for the iontophoresis system into which it is connected.

An advantage is to provide such a device capable of maintaining voltage at a stable level for a determined known charge dosage, afterwards having an automated ability to adjust the voltage downward or upward to at least a second known voltage and determined charge dosage in rapid fashion, without a microprocessor or other outside control.

A further advantage is the provision of a multi-couple galvanic power system which can be adjusted to higher voltage during use, in order to administer a bolus of medication.

Another advantage resides in a multi-couple, time-variable galvanic power system employing several serially connected galvanic sources of different coulombic capacities in conjunction with parallel or serial connected resistor devices.

Materials used are not reactive in contact with water, w and are stable when used in a manufacturing process.

Other objects and advantages will occur to those skilled in the art upon familiarization with this specification, drawings and appended claims.

SUMMARY OF THE INVENTION

An iontophoretic patch in accordance with the invention includes, in its simplest form, at least three chambers: a cationic drug chamber, an anionic drug chamber, and an additional galvanic source or cell otherwise known as a galvanic couple or galvanic couple power source. The system may also have a series of such cells together with one or more parallel or serial connected resistance devices or other components in more complex versions. In the cationic drug chamber, an electrode is contained which includes or is coated with, an electrochemically oxidizable species. In the anionic drug chamber, an electrode is contained which includes or is coated with, an electrochemically reducible species. The chambers are separated by a known distance optimally between 0.1 and 2 cm. The cationic chamber electrode and the anionic chamber electrode are connected by electrically conductive elements to an additional intermediate electrochemical cell or cells. Opposing ends of the electrically conductive elements, which extend to the intermediate cell or cells, are comprised of, or coated with, reductive species if the end opposite is oxidative, or oxidative species if the end opposite is reductive.

The net result is a series connection of galvanic couples or sources, which serve to boost the applied potential of the iontophoretic system. Embodiments employing an illustration of an iontophoretic system using zinc as the oxidative species and silver chloride as the reducible species, having one intermediate chamber or galvanic source and providing an applied potential of approximately 2 volts and also using two intermediate chambers or galvanic sources and providing an applied potential of approximately 3 volts are shown in the drawings to illustrate the concept without limitation. The total applied potential of the galvanic system of this invention is directly correlated to the number of intermediate chambers utilized. It will be apparent that the number of intermediate galvanic sources or couples can be varied depending on the desired total potential.

An important aspect of the invention that enables high dosage rating accuracy for the iontophoretic patch devices is that the manufacturing process includes characterizing the charge capacity of batches or lots of the galvanic power sources or components (half-couples) in accordance with actual manufactured capacity rather than a target capacity. The capacity of the typical corresponding couple can be predicted with a greater degree of accuracy and any iontophoresis patch using one or more of these characterized galvanic power sources will also have (within close tolerances) a known capacity such that it may be designated or labeled as such. Thus, a batch or lot as per the examples I–III below, could be labeled in accordance with test results as 80 mA-minutes ±10% per inspection, sampling and testing procedures using the examples with a high degree of confidence. An untested lot with a target capacity of 80 mA-minutes may in fact be well outside these characterization limits. This added confidence enables the galvanic power sources not only to be the sole power sources for the iontophoresis patch, but also to provide the only necessary dosage control for that patch.

In addition, one or more resistor devices can be connected in parallel with one or more of the galvanic sources. This assures serial operation of multiple source systems while all sources are operating and provides paths across depleted cells of lesser capacity in the system so that a therapeutic agent can continue to be administered at a lower rate.

One or more resistor devices can also be connected in series with the galvanic sources. This configuration allows for a limiting of current flow through the system when applied to a patient. This series resistance can also serve to normalize the variations in current flow in systems placed on different patients or in different body locations due to natural variations in skin impedance.

One or more switching devices can be provided in the iontophoretic patch to switch one or more of the intermediate sources or chambers into the circuit or to bypass or shunt one or more galvanic sources as desired. A switching device rather than a resister can also be used to by-pass a depleted galvanic source without added circuit resistance if it is desired to provide an initial bolus of therapeutic material, all serially connected sources or cells can be employed for an initial period and one or more configured to deplete and thereby reduce the potential at a later time.

Thus, one or more of the intermediate chambers can be made anode or cathode limited in a manner which causes depletion at a time when the desired bolus of initial material has been delivered. Parallel resistors or switches, then, provide a conductive path to enable delivery to continue at a lower rate. Switching devices can also be employed which shut off the entire galvanic flow in the iontophoretic patch or to switch in additional series connected galvanic sources as by opening by-pass conductor circuits for example.

In yet another type of configuration, galvanic sources can be serially connected in opposed polarity such that a lower capacity source opposes a therapeutic or agent delivery source to initially delay agent delivery until the lower capacity source is depleted.

The oxidizable species and the reducible species are selected so as to provide a spontaneous galvanic potential and current flow when the iontophoretic patch is in contact with the body. An example of a suitable oxidizable species is zinc and a suitable reducible species is silver chloride. While this combination may be advantageous for many applications, it is not meant as a limitation as the scope of the invention but is presented only by way of example.

During the iontophoretic process of this invention, as current flows, the oxidizable species in the cationic drug chamber and one or more intermediate cells become oxidized, while the reducible species in the anionic chamber and intermediate cells become reduced. The galvanically induced current will continue to flow until depletion of either the oxidizable or reducible species, whichever is present in limiting amount. The relationship between the amount of current flow and the amount of oxidizable or reducible species in limiting supply, is theoretically represented by Faradays constant; one gram equivalent of the limiting reducible or oxidizable species will provide one Faraday (96,487 coulombs) of electricity. The iontophoretic patch of this invention will optimally deliver a fixed and known charge in a range between about 0.06 and 60 coulombs, which corresponds to between 0.00000062 and 0.00062 gram equivalent weight of oxidizable or reducible species in limiting supply.

Other circuit elements may also, be created using thin film, screen printing or other such methods in accordance with state-of-the-art techniques.

Other aspects of the patch include an impervious backing material, which can be constructed with 3M polyethylene tape #1523, #1526, (available from 3M Corporation, St. Paul, Minn.) or other occlusive material. Holding the electrodes in place, and attached to the backing material is a cell wall defining layer, which has separated openings to define anode and cathode cell cavities, as well as intermediate chamber cavities. The cell wall defining layer can be constructed of 3M #1772 or similar material. An absorbent layer is added to each of the cavities defined by the cell wall defining layer, and serves to retain fluid in the cell cavity. The absorbent layer can be a material which forms a gel when contacted with aqueous solution such as polyacrylamide, or it can be cotton, gauze, or other hydrophilic material. An adhesive layer is used to fix the iontophoretic device to the skin, which can also be comprised of materials such as 3M #1523 or #1526.

To use the controlled dosage iontophoresis device, as shown in FIG. 1, solution containing cation to be delivered is put into the cationic drug chamber, and solution containing anion material is injected into the anionic drug chamber. The intermediate chamber is preferably filled with a conductive salt solution, through an access port on either the top or bottom of the device. Optionally, the intermediate chamber can be pre-filled with a salt-containing gel or paste. Unlike the Anionic and Cationic Drug Chambers, the intermediate chamber or source or sources should not be in contact with the skin. The patch is then applied to the portion of the body where drug is to be administered, and adhered to the skin by an adhesive layer on the bottom of the patch and or by an overlaying bandage material. Once contacted with skin, an electrical circuit is completed which allows passage of current and delivery of drug compounds.

DETAILED DESCRIPTION

Figure 1:
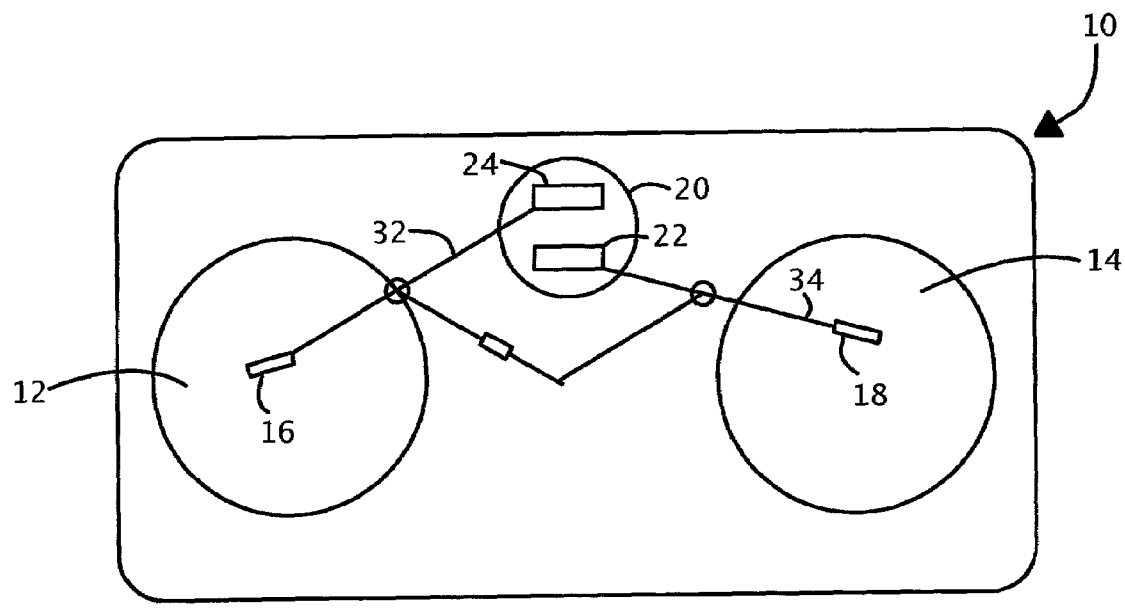
FIG. 1 is a schematic illustration of a galvanic iontophoretic system in accordance with the invention having a primary galvanic couple or source and one intermediate chamber having a second galvanic couple or source.

The detailed description of the present invention illustrates the principles of an advanced multi-source, multi-rate galvanic transdermal drug delivery system which has the ability to use time varying rates. The embodiments are described by using a very limited number of example configurations and material compositions, including therapeutic agents delivered. It is believed that the application of the principles encompassed by the present inventive concept, however, are much broader and, in reality, many configurations of primary and intermediate or therapeutic agent containing or additional galvanic sources or chambers, resistor elements or devices and other circuit elements together with a great number of conductors, galvanic couples (oxidizable and reducible species), therapeutic agents to be delivered and actual configurations of the wearable patch are possible. Accordingly, the descriptions and accounts given herein are intended as examples and not meant to limit the scope of the invention in any manner. Terms such as galvanic source, galvanic chamber, galvanic couple, are used interchangeably.

As previously indicated, the transdermal or skin applied wearable patches produced in accordance with the present invention are normally designed to remain in a dry state until used. This greatly extends useful shelf life and insures the use of fresh drug and electrolyte solutions.

FIGS. 1, 2 and 6–8 of the drawings are intended to depict schematically some iontophoretic systems illustrating principles of the multi-source, multi-rate, time-variable, galvanic concept of the invention. A schematic representation of an iontophoretic wearable patch is shown at 10 which includes a primary dual chamber galvanic couple including a cationic drug chamber 12 and an anionic drug chamber 14. The cationic chamber 12 contains a source of oxidizable material 16, which may be zinc; and the anionic chamber contains a source of reducible material 18, which may be silver chloride. A first additional or intermediate chamber or source 20 is located between chambers 12 and 14, itself containing a source of oxidizable material 22, which may be the same (Zn) or a different material from the material 16 and a source of reducible material 24, which may be the same (AgCl) or a different material from the material 18. These are contained in a conductive relation in the intermediate chamber.

Figure 2:
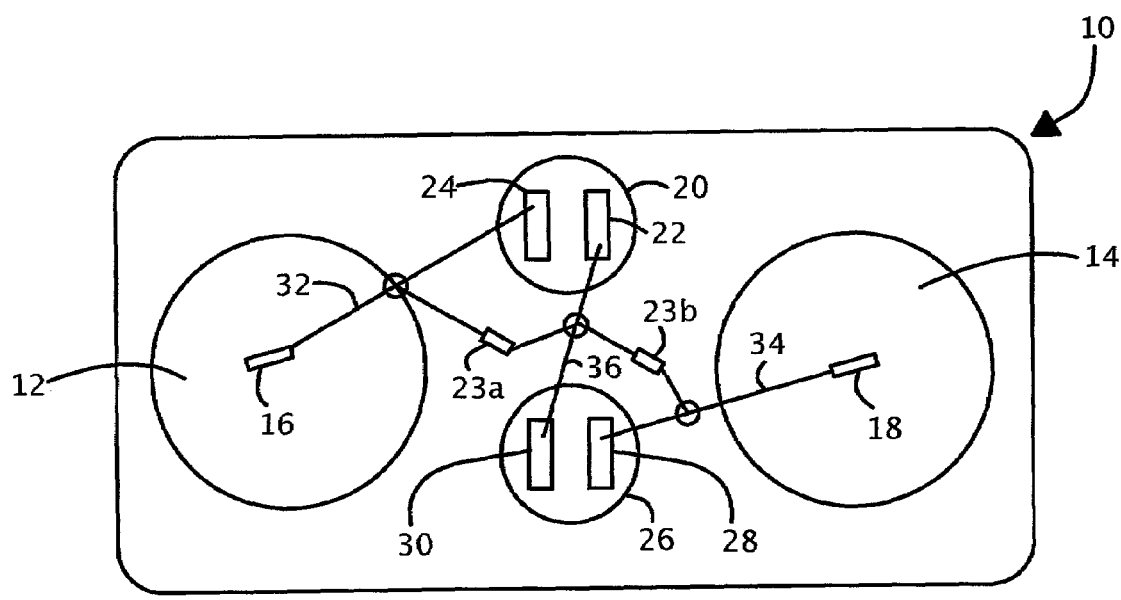
FIG. 2 is a schematic illustration of a galvanic iontophoretic system similar to that of FIG. 1 having a primary galvanic couple or source and two intermediate chambers or sources.

FIG. 2 shows the iontophoretic system of FIG. 1, but including a second intermediate chamber 26 containing a source of oxidizable material 28 and a source of reducible material 30 which may be the same as or different from those used in intermediate chamber 20. Conductors 32, 34, respectively, connect the electrodes 16, 24; and 22, 28 in chambers 12, 20 and 14 in series in FIG. 1. An additional intermediate conductor 36 is provided in FIG. 2 to serially connect the intermediate chambers 20 and 26. An optional resistor device 23 is shown connected in phantom between conductors 32 and 34 in FIG. 1 in parallel with the galvanic sources (12, 14) and 20 and a pair of optional resistive devices 23a and 23b are shown connected in parallel with the two intermediate sources 20 and 26 in FIG. 2. If used the resistors cause the sources to operate in series while all sources are active and provide continuity to the circuit when the parallel connected source becomes depleted. The value of example resistor devices 23, 23a and 23b can be as desired but may typically be about equal to skin resistance or generally in the 1 K ohm to 100 K ohm range and typically about 10 K ohm.

Figure 7A:
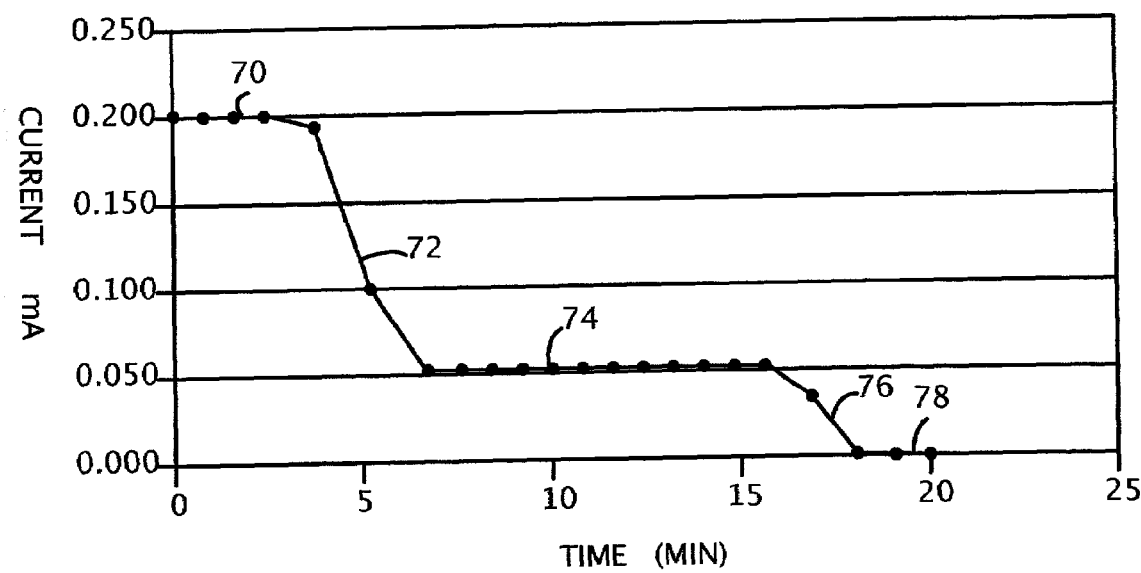
FIGS. 7a and 7b depict a graphical representation and circuit schematic of using one additional source and a parallel resistance approximating skin resistancy.
Figure 7B:
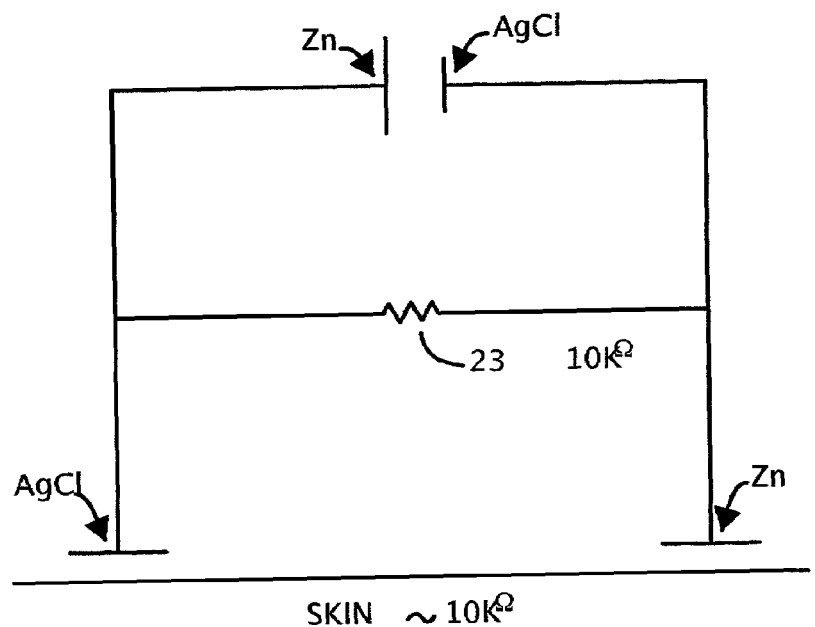

FIG. 7b depicts a simple circuit schematic for the schematic iontophoresis device illustrated in FIG. 1 in which the resistance 23 is approximately 10 Kohms which is generally equivalent to the average skin resistance experienced by patch devices used for iontophoretic transfer.

FIG. 7a graphically represents the operation of the schematic device illustrated in FIG. 7b, note the high initial delivery bolus 70 which rapidly diminishes at 72 with the depletion of the couple 22/24 at 72 to a value at 74 approximately ¼ of the original value and as much as the potential has been cut in half and the resistance double when the serial resistor 23 is added in. Another deep drop-off occurs at 76 when the couple 16, 18 is depleted and the transmission quickly falls to 0 at 78. This, then, illustrates one embodiment in which a higher dosage of medication is administered at the outset or beginning of a treatment followed by a lower dosage for a longer period of time. This drug delivery profile is appropriate for an application where it is desirable to reach a therapeutic level as quickly as possible in the body followed by a lower drug delivery rate that is adequate to maintain a drug level in the body just slightly above the therapeutic level for a longer period of time.

Figure 9:
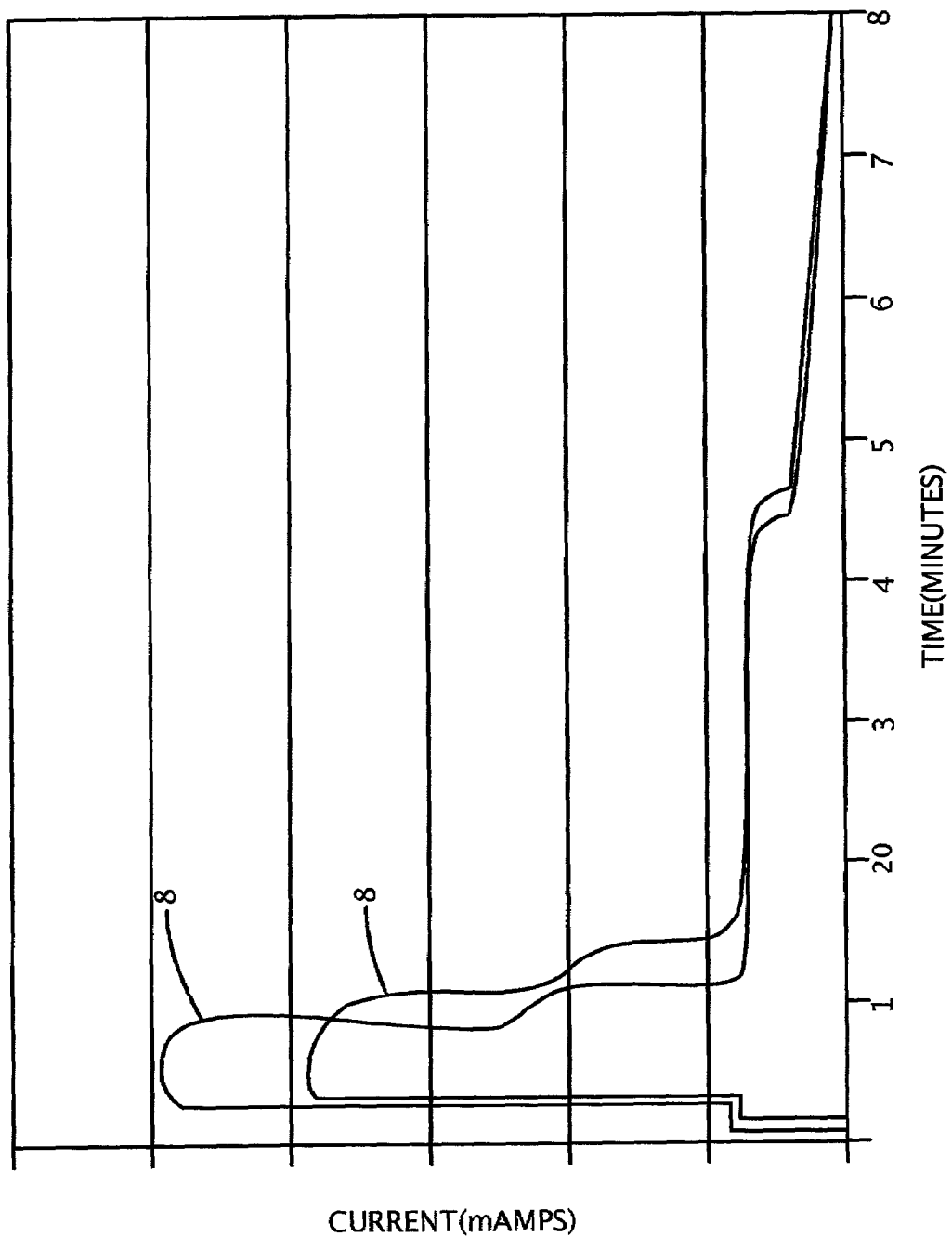
FIG. 9 represents actual laboratory data taken using the configuration of FIG. 7b.

FIG. 9 represents actual laboratory data derived form a configuration similar to that shown in FIGS. 1 and 7b. While there are certain differences between the curves 80 and 82 in that figure, they clearly indicate the administration of the initial bolus of higher rate of infusion followed by a longer period of at a lower rate and finally by an extinguishments of the current flow.

Figure 8A:
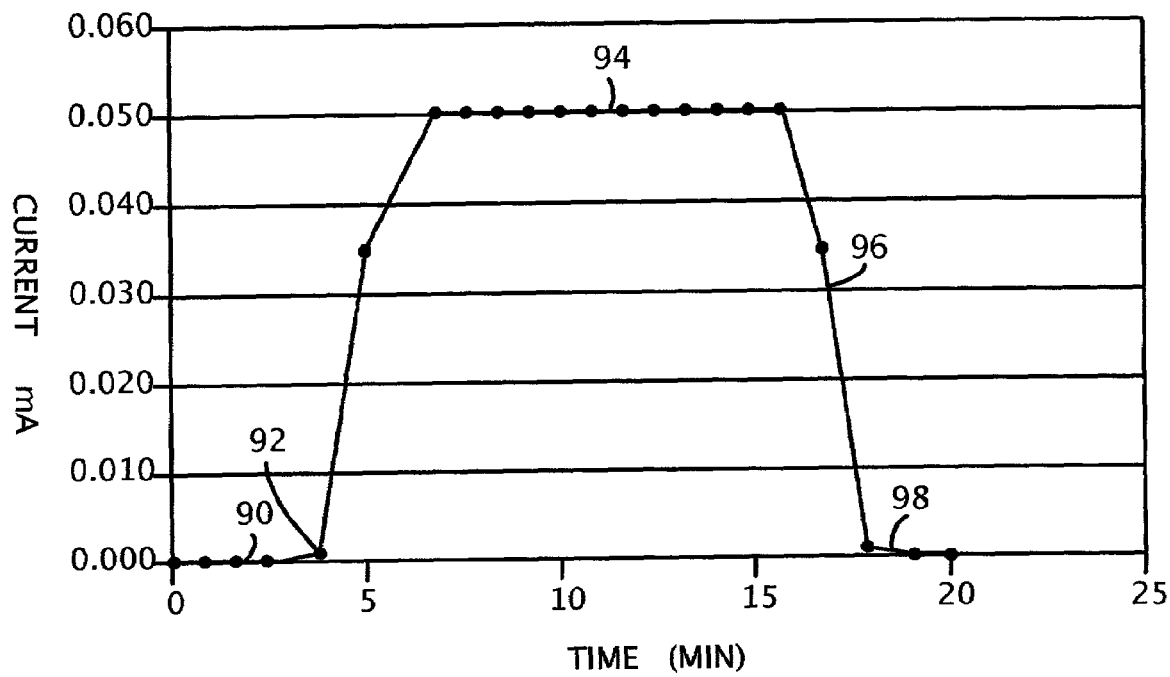
FIGS. 8a and 8b are similar to FIGS. 7a and 7b for a configuration in which the polarities of the sources are opposed.
Figure 8B:
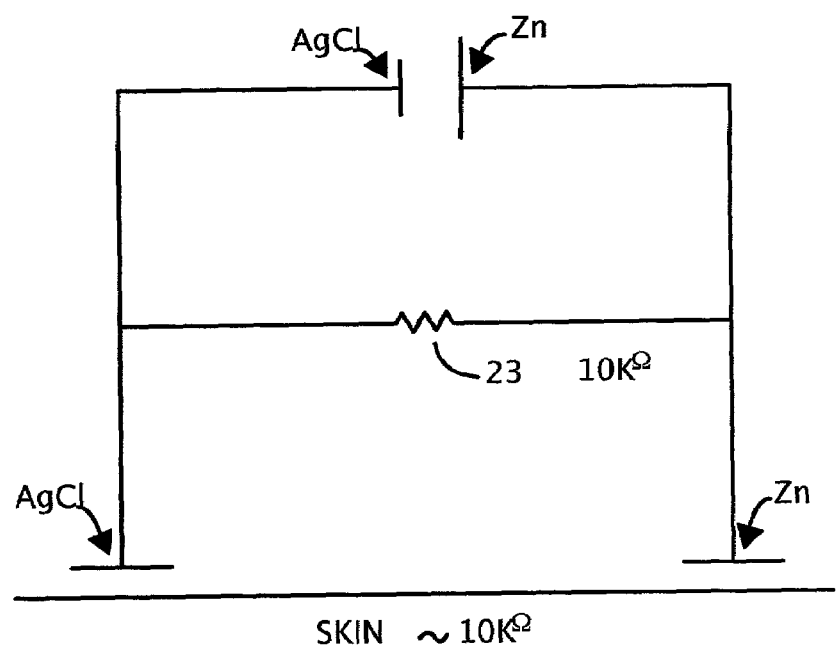

Finally we see FIG. 8b representing a circuit similar to those of FIG. 1 and FIG. 7b except that the second or additional source 22, 24 is connected in opposite polarity so that current generated by 22, 24 opposes that generated by 16, 18 as shown at 90 in FIG. 8a, this results initially in the absence of net current flow in the skin connected branch of the circuit such that no iontophoretic transfer takes place until the depletion of the anode or cathode of couple 22, 24 at 92 after which the delivery current rapidly rises to 0.05mA where it remains substantially constant throughout the remainder of the life primary or agent delivering couple 16, 18 at 94. The depletion of an electrode in the agent delivering couple 16/18, the current again rapidly drops at 96 to 0 at 98.

It becomes apparent even from the small number of examples presented that one skilled in the art could arrive at a great many variations in electronic circuit design to construct a circuit that would produce almost any imaginable drug delivery profile one would desire based on the current-time profiles possible. Thus, series and parallel combinations are possible with almost any number of cells and resistors, keeping in mind that the cells can have different coulombic capacities and external resistances can be varied. It should further be noted that additional time can be added to the delivery by using additional cells in parallel rather than in series.

Figure 3:
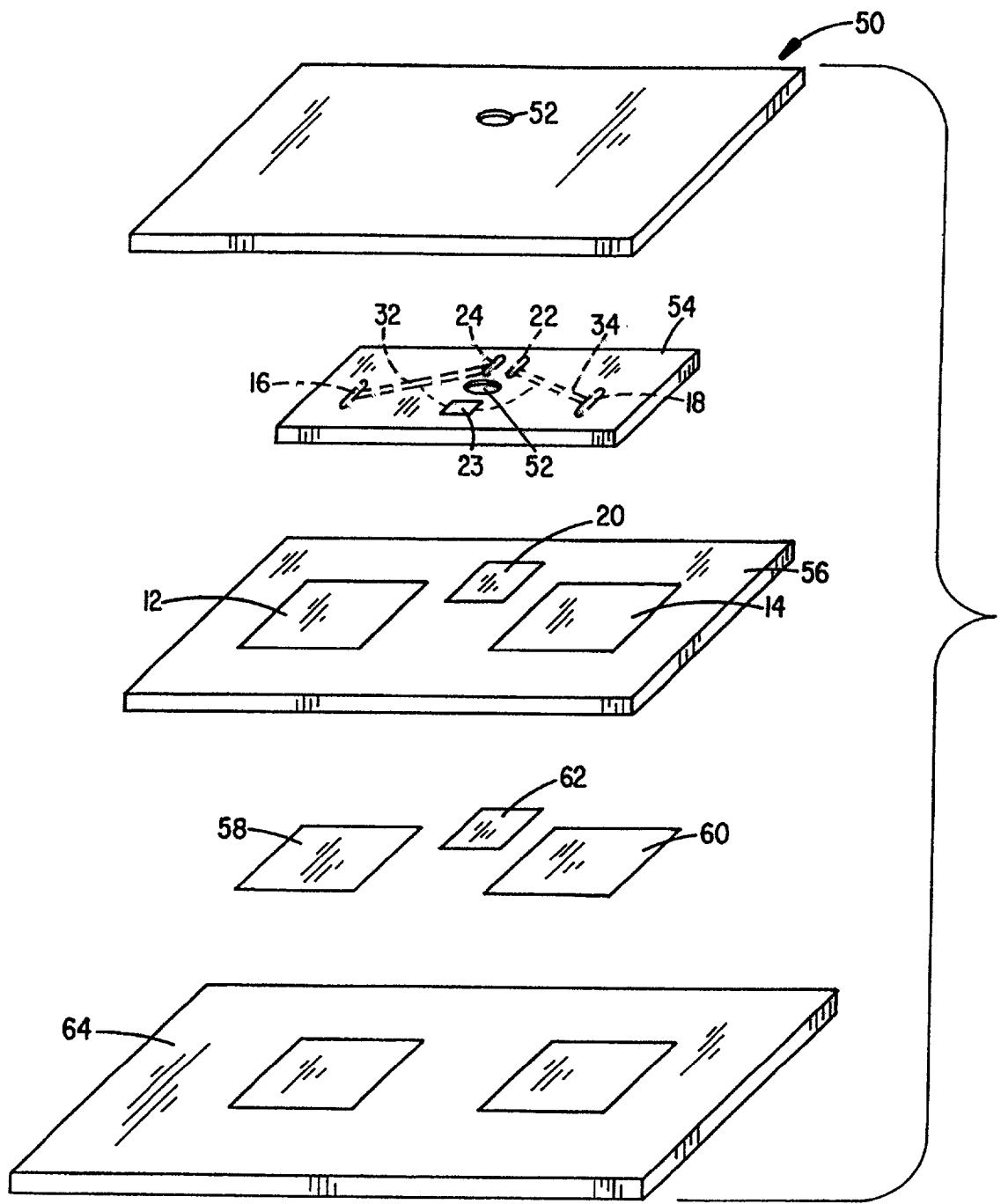
FIG. 3 is an exploded or blown apart drawing showing the assembly of an iontophoretic patch embodiment that includes a screen printed circuit system for an embodiment similar to that in FIG. 1.

The exploded view of FIG. 3 illustrates one preferred approach to the preparation of the iontophoretic electrode and conductor system for an embodiment similar to that illustrated in FIG. 1. It includes a layer of backing material layer 50, which may be constructed with material such as 3M polyethylene tape #1523, #1526 or other such occlusive membrane, an intermediate cell fill port is shown at 52. A dual galvanic source battery system is shown printed on a flex circuit screen layer 54 beneath the backing layer 50. A cell wall defining layer is shown at 56 and absorbent layers for the chambers are shown at 58, 60 and 62. The final bottom adhesive layer is shown at 64.

Figure 4:
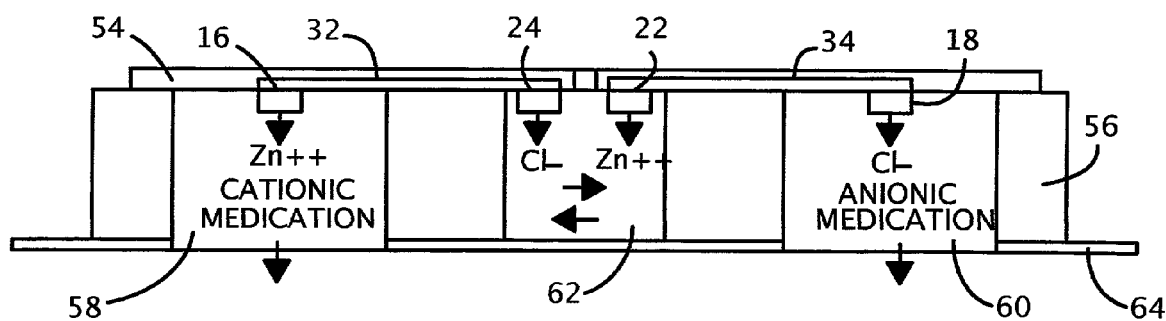
FIG. 4 shows, in crossection, a schematic illustration of ion flow in a one intermediate source version of the invention similar also to that in FIG. 1.

The cross sectional drawing of FIG. 4 illustrates the flow of electrons and ions during use of a one intermediate chamber version of this invention similar to that represented by FIG. 1 and so the same reference numerals can be employed. The intermediate chamber or source 20 may have a useful life that is the same or shorter than that of the primary couple 12, 14. In this manner, the intermediate source 20 will boost the rate of transfer by the primary couple 12, 14 will control the amount such that when either the oxidizable material of the cationic drug chamber electrode 16 is depleted, or the reducible material of the anionic drug chamber electrode 18 is depleted, current flow falls to essentially zero and the delivery of drug compound is completed.

Figure 5:
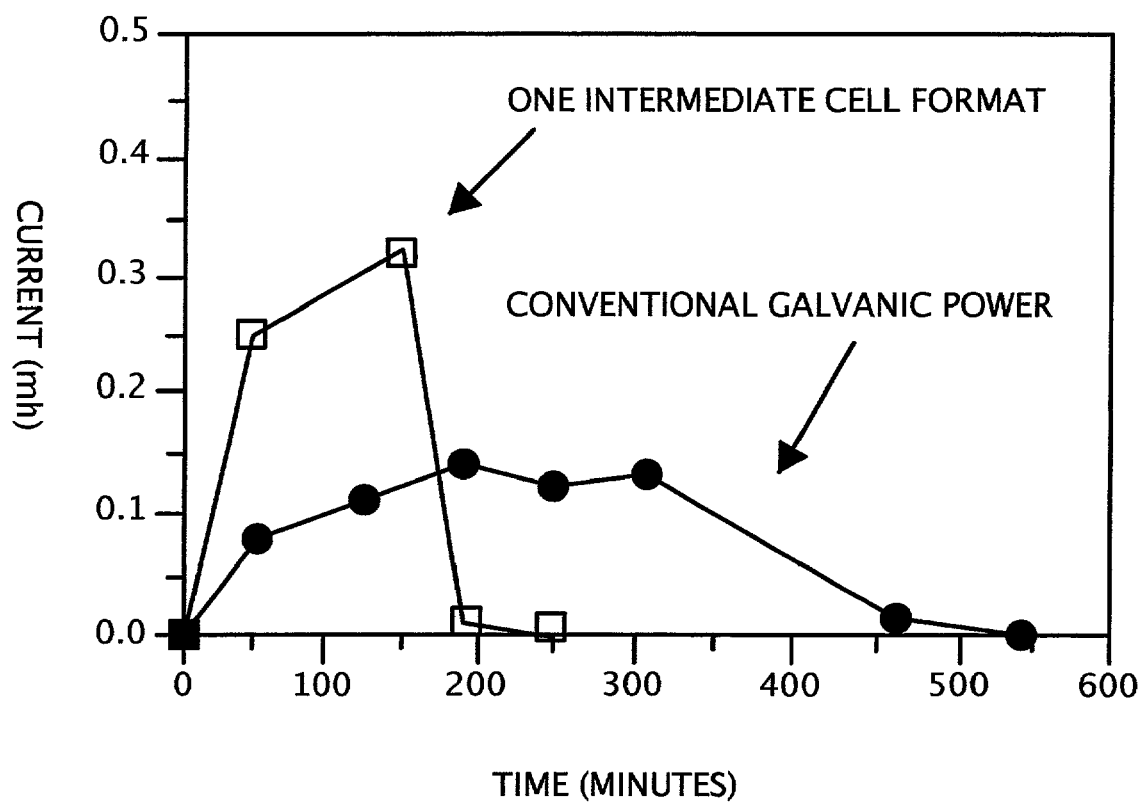
FIG. 5 shows comparison current-time profile plot between a one intermediate source version of the present invention and a conventional galvanic system without an intermediate galvanic source.

FIG. 5 illustrates the fixed delivery of current as a function of time from a battery prepared in accordance to this invention. In this experiment, a limiting supply of zinc serves as the oxidizable species, the reducible species was silver chloride, and one intermediate cell was used. For comparison purposes, a current-time profile of a conventional galvanic system is charted as well, also using zinc as an oxidizable species in limiting supply and silver chloride as the reducible species. As shown, the current level (and consequently the medication delivery rate) is higher in this invention, owing to a higher application voltage (2 volts vs. 1 volt).

Figure 6:
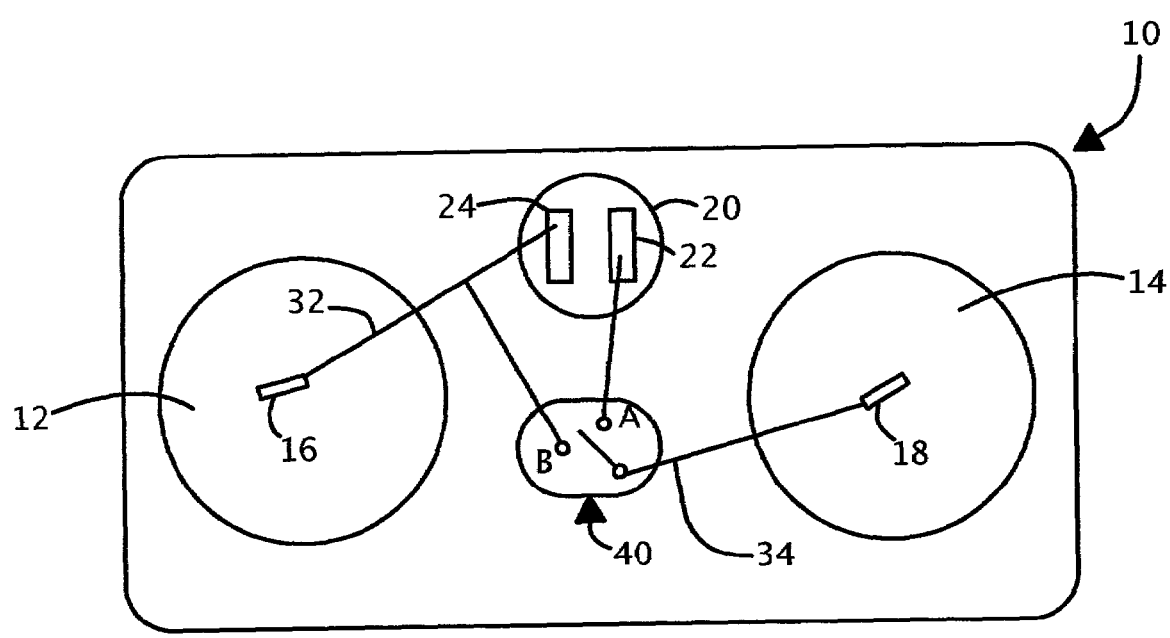
FIG. 6 shows an illustration including a switch mechanism in conjunction with the system of FIG. 1 to enable manually adjustable higher and lower voltage activation and an off setting.

FIG. 6 is an illustration of the invention similar to FIG. 1 with an integrated switch, again using zinc and silver chloride as the oxidizable and reducible species. Activation of the switch in "A" position allows a high application voltage (in this case to 2 volts) and higher medication flow. Adjustment of the switch to the "B" position reduces voltage (in this case to 1 volt) and to a lower medication flow. In addition, this shows how this invention can be modified to allow manual adjustment of medication flow between high and low flow rates with a simple switch assembly. In addition, the current flow may be shut off in the illustrated neutral position.

Preparation of the iontophoretic electrodes of this invention is critical, as a known limiting amount of electroactive species is targeted to be incorporated within, or onto, any anode electrode, any cathode electrode, or multiple electrodes. In preparation of the cationic drug chamber electrode, ideally oxidizable material can be used of known weight and purity; or an oxidizable coating of known amount can be deposited on the surface of an electrically conductive substrate. For example, ideally a target amount of molten zinc can be deposited over a wire substrate, to produce an electrode with known oxidizable species content. Likewise, a target amount of a reducible material of known amount can be deposited on the surface of an electrically conductive substrate; for example, ideally a target amount of molten silver chloride can be deposited over a wire substrate, to produce an electrode with known reducible species content. Alternatively, a target amount of silver chloride can be generated on the electrode surface by an electrolytic or electroplating process, such as by electrolytic oxidation of a silver wire in the presence of chloride, to produce a coating of silver chloride.

While these targeted, ideal goals can be approached in theory, the cells or galvanic couples of the invention are typically produced in rather large lots or batches of from about 25,000 cells or half-cells to 500,000 or even 1,000,000 cells. Processing may be done, for example, using sheets or on rolls of substrate or release material As used herein, the terms "lot" or "batch" refers to any acceptable type of process in which a given number of devices or cells are separately identified as a manufactured group. Variations in cell capacities both within a given batch and from batch to batch do vary even with very tight manufacturing tolerances. According to the invention, however, it has been discovered that characterizing a lot or batch according to actual measured capacity based on testing using acceptable sampling standards, however, does produce an accurate average measure of capacity.

As indicated, an important aspect of the present invention involves the manufacture of the galvanic power source couples or cells and half cells utilized in the iontophoresis patches and more particularly to a method in which the cells of a lot or batch of cells are characterized in terms of actual manufactured capacity rather than any target capacity. This enables, in turn, a sufficient capacity predictability in devices using such cells that the capacity of the resulting patches may be labeled with a high degree of confidence.

The power sources of the present invention may be fabricated by conventional means using paste-type materials in conjunction with well known screen printing and baking (drying) processes. While this enables generally accurate layer thicknesses to be produced, the results can vary somewhat from batch to batch and also across the area of the same batch. Thus, although the power sources may be intended to be built to a particular capacity, unless the capacity of the power sources or source components of the batch or lot is adequately tested, the actual capacity cannot be accurately predicted. Accordingly, it has been found that an adequate amount of testing is required to properly characterize the charge capacity a given process lot of cells or half cells in order that the dosage of corresponding iontophoretic devices employing these components can be reliably designated or labeled.

The following tables represent examples of lots of representative sampling test results for lots or batches of galvanic couple cells or half-cells tested to exhaustion.

The sampling procedure used is meant to be representative, it being realized that other acceptable methods exist and could be used.

Testing has been done in accordance with American National Standard Sampling Procedures and Tables for Inspection by Variables for Percent Non-Conforming, prepared by American Society for Quality Control Standards Committee for American National Standards Committee Z-1 on Quality Assurance. This is an acceptable sampling procedure to be used on a continuing stream of lots for AQL specified. It provides tightened, normal and reduced plans to be used on measurements which are normally distributed. Variations may be measured by sample standard deviation, sample range or known standard deviation. The present revision is known as ASQ/ANSI Z1.9-1993 corresponds directly to the military standard MIL-STD-414. That spec is based on the following inputs:

Inspection Level-II

Normal Inspection AQL=1.5%

Variability Unknown

Double Spec Limit (±10%)

For lot sizes between 10,000 and 35,000, the sample size is n=100. For lot sizes between 35,001 and 150,000, the sample size will be n=150. For lot sizes between 150,001 and 500,000, the sample size will be n=200.

EXAMPLE I

Lot Size 26,994

| | |
|---|---|
| Sample Size | 100 |
| Average | 77.65 |
| Standard Deviation | 2.49 |
| Estimated Percent Nonconforming Above Upper Limit | 0 |
| Estimated Percent Nonconforming Below Lower Limit | 1.087 |
| Estimated Total Percent Nonconforming | 1.087 |
| Maximum Allowable Percent Nonconforming | 3.06 |
| Meet Specification? Yes or No | — |
| Will Trimming Reduce Percent nonconforming? Yes or No | NA |

EXAMPLE II

Lot Size 70,000

| | |
|---|---|
| Sample Size | 150 |
| Average | 79 |
| Standard Deviation | 3.5 |
| Estimated Percent Nonconforming Above Upper Limit | 0.473 |
| Estimated Percent Nonconforming Below Lower Limit | 2.22 |
| Estimated Total Percent Nonconforming | 2.69 |
| Maximum Allowable Percent Nonconforming | 2.88 |
| Meet Specification? Yes or No | — |
| Will Trimming Reduce Percent nonconforming? Yes or No | |

EXAMPLE III

Lot Size 187,640

| | |
|---|---|
| Sample Size | 200 |
| Average | 78.9 |
| Standard Deviation | 3.5 |
| Estimated Percent Nonconforming Above Upper Limit | 0.441 |
| Estimated Percent Nonconforming Below Lower Limit | 2.40 |
| Estimated Total Percent Nonconforming | 2.841 |
| Maximum Allowable Percent Nonconforming | 2.86 |
| Meet Specification? Yes or No | — |
| Will Trimming Reduce Percent nonconforming? Yes or No | NA |

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A method of providing power sources and dosage control systems having reliable capacity ratings for transdermal iontophoresis delivery of therapeutic agents, said power source and dosage control systems comprising a plurality of serially connected galvanic couple power sources, the method comprising steps of:

(a) manufacturing one or more lots of galvanic couple power sources;

(b) determining by sample testing capacity characteristics including an average charge capacity for said galvanic couple power sources of each of said one or more lots to produce tested lots;

(c) serially connecting a plurality of said galvanic couple power sources selected from one or more tested lots into power source and control systems;

(d) incorporating said power source and control systems into transdermal iontophoresis therapeutic agent delivery devices as the sole sources of power and delivery control; and (e) providing labeling indicating average capacity for said agent delivery devices based on the tested average charge capacities of corresponding tested lots from which said plurality of galvanic power sources are taken.

2. A method as in claim 1 comprising the further step of connecting one or more resistance devices in parallel with one or more of said plurality of galvanic power sources.

3. A method as in claim 1 including the step of providing for one or more of said galvanic power sources expire at a different time.

4. A method as in claim 3 further comprising the step of connecting a resistance device in parallel with one or more of said plurality of galvanic power sources.

5. A method as in claim 3 comprising the step of providing a pair of said galvanic power sources in opposed polar relation and in parallel with a resistor device such that iontophoretic delivery current flows to deliver said therapeutic agent only after one source expires.

6. A method as in claim 3 further comprising the step of connecting a switch device across a galvanic power source designed to expire before at least one other.

7. A method as in claim 1 further comprising the step of connecting a switch device across one or more of said serially connected galvanic power sources.

8. A method as in claim 1 wherein said sample testing comprises the step of reacting galvanic sources or half-cells to exhaustion.

9. A method as in claim 1 wherein said plurality of galvanic couple power sources are selected from the same tested lot.

10. A method as in claim 1 wherein said plurality of galvanic couple power sources are selected from a plurality of tested lots.

11. A method as in claim 1 wherein said delivery device is a wearable skin patch.

12. A method as in claim 11 further comprising the step of packaging said delivery device in a dry state separate from said therapeutic agent.

13. A method as in claim 1 further comprising the step of packaging said delivery device in a dry state separate from said therapeutic agent.

14. A method of providing an accurate average available dosage rating for labeling skin-worn transdermal iontophoresis therapeutic agent delivery devices having self-contained combined power source and dosage control systems including a plurality of galvanic couple sources, including steps of sampling and testing average power capacities of lots from which said plurality of galvanic power sources are taken, using test results to determine an average available dosage and labeling said device in accordance with said average available dosage rating.

15. A transdermal iontophoresis therapeutic agent delivery device comprising:

(a) a plurality of self-contained serially connected galvanic power sources, wherein said plurality of galvanic power sources alone provide the power for the device and the control for the rate and dosage of therapeutic agent delivered;

(b) said plurality of galvanic power sources including provision for one or more of said sources to expire at a different time; and (c) a resistance device connected in parallel with one or more of said galvanic power sources.

16. A device as in claim 15 in the form of a wearable skin patch.

17. A transdermal iontophoretic therapeutic agent delivery device as in 15 further comprising a label associated with said delivery device identifying the capacity of said delivery system and that said capacity is based on the average tested, capacities of corresponding manufactured lots of said plurality of galvanic power sources.

18. A device as in claim 17 in the form of a wearable skin patch.

19. A device as in claim 17 wherein said device is stored in a therapeutic agent-free state until used.

20. A device as in claim 17 having two galvanic power sources.

21. A device as in claim 20 comprising a pair of said galvanic power sources in opposed polar relation and in parallel with a resistor device such that iontophoretic delivery current flows to deliver said therapeutic agent only after one source expires.

22. A device as in claim 21 further comprising a switch connected across one or more of said serially connected galvanic sources.

23. A device as in claim 17 wherein said plurality of galvanic power sources includes one or more sources selected to have significantly lower charge capacity.

24. A device as in claim 23 wherein said device is stored in a therapeutic agent-free state until used.

25. A device as in claim 15 having two galvanic power sources.

26. A device as in claim 25 comprising a pair of said galvanic power sources in opposed polar relation and in parallel with a resistor device such that iontophoretic delivery current flows to deliver said therapeutic agent only after one source expires.

27. A device as in claim 15 further comprising a switch connected across one or more of said serially connected galvanic sources.

28. A device as in claim 27 wherein a switch is connected across a galvanic power source designed to expire before at least one other.

29. A device as in claim 28 including a three-position switch.

30. A device as in claim 27 including a three-position switch.

* * * * *